United States Patent
Mitchell et al.

(10) Patent No.: US 9,701,662 B2
(45) Date of Patent: Jul. 11, 2017

(54) HERBICIDAL COMPOUNDS

(71) Applicant: Syngenta Participations AG, Basel (CH)

(72) Inventors: Glynn Mitchell, Bracknell (GB); Nicholas Phillip Mulholland, Brackenll (GB)

(73) Assignee: Syngenta Participations AG, Basel (CH)

(*) Notice: Subject to any disclaimer, the term of this patent is extended or adjusted under 35 U.S.C. 154(b) by 0 days.

(21) Appl. No.: 15/120,863

(22) PCT Filed: Feb. 26, 2015

(86) PCT No.: PCT/EP2015/054041
§ 371 (c)(1),
(2) Date: Aug. 23, 2016

(87) PCT Pub. No.: WO2015/128424
PCT Pub. Date: Sep. 3, 2015

(65) Prior Publication Data
US 2017/0066745 A1   Mar. 9, 2017

(30) Foreign Application Priority Data

Feb. 27, 2014 (GB) .................................. 1403495.3

(51) Int. Cl.
*C07D 403/12* (2006.01)
*A01N 43/713* (2006.01)
*A01N 43/653* (2006.01)

(52) U.S. Cl.
CPC ......... *C07D 403/12* (2013.01); *A01N 43/653* (2013.01); *A01N 43/713* (2013.01)

(58) Field of Classification Search
CPC ... C07D 403/12; A01N 43/713; A01N 43/653

USPC .......................................... 504/137; 514/381
See application file for complete search history.

(56) References Cited

FOREIGN PATENT DOCUMENTS

| EP | 1982978 A1 | 10/2008 |
|---|---|---|
| EP | 2562174 A1 | 2/2013 |
| WO | 2013144234 A1 | 10/2013 |
| WO | 2013164333 A1 | 11/2013 |

OTHER PUBLICATIONS

International Search Report for International Application No. PCT/EP2015/054041 mailed on Mar. 26, 2015.

*Primary Examiner* — Johann R Richter
*Assistant Examiner* — Andriae M Holt
(74) *Attorney, Agent, or Firm* — James Cueva

(57) ABSTRACT

The present invention relates to compounds of Formula (I), or an agronomically acceptable salt of said compounds wherein A1, A2, $R^1$, $R^2$, $R^3$ and $R^4$ are as defined herein. The invention further relates to herbicidal compositions which comprise a compound of Formula (I), to their use for controlling weeds, in particular in crops of useful plants, and to intermediates used to synthesize said compounds.

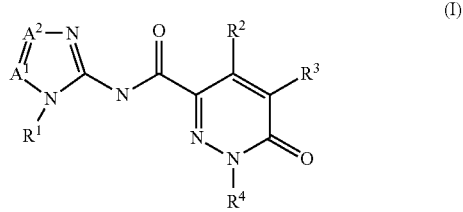

15 Claims, No Drawings

HERBICIDAL COMPOUNDS

RELATED APPLICATION INFORMATION

This application is a 371 of International Application No. PCT/EP2015/054041, filed Feb. 26, 2015, which claims priority to GB Application No. 1403495.3, filed Feb. 27, 2014, the contents of which are incorporated herein by reference herein.

The present invention relates to novel herbicidal compounds, to processes for their preparation, to herbicidal compositions which comprise the novel compounds, and to their use for controlling weeds, in particular in crops of useful plants, or for inhibiting plant growth.

Herbicidal 6-oxo-1,6-dihydropyrimidin-5-carboxamides are reported in EP-A-2562174. Herbicidal 6-pyridone-2-carbamoyl-azoles are disclosed in WO2013/164333. The present invention relates to novel herbicidal pyridazinone compounds.

Thus, according to the present invention there is provided a compound of Formula (I):

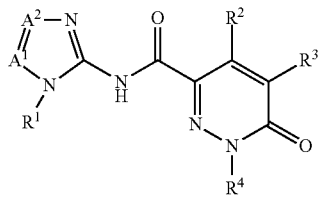

or an agronomically acceptable salt thereof,
wherein:—
$A^1$ and $A^2$ are independently selected from CH and N, wherein $A^1$ and $A^2$ are not both CH;
$R^1$ is selected from the group consisting of $C_1$-$C_6$alkyl-, $C_1$-$C_6$haloalkyl- and $C_1$-$C_6$alkoxy-$C_1$-$C_3$alkyl-;
$R^2$ is selected from the group consisting of halogen, —$NHR^5$ and —O—$R^6$;
$R^3$ is selected from the group consisting of hydrogen, halogen, $C_1$-$C_6$ alkyl, $C_1$-$C_6$ haloalkyl-, $C_1$-$C_6$alkoxy-$C_1$-$C_3$alkyl-, benzyl and phenyl, wherein the benzyl and phenyl are optionally substituted with one or more substituents selected from the group consisting of halogen, $C_1$-$C_6$ alkyl, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-;
$R^4$ is selected from the group consisting of $C_1$-$C_6$ alkyl, $C_3$-$C_6$-cycloalkyl and $C_1$-$C_6$ haloalkyl-;
$R^5$ is selected from the group consisting of $C_1$-$C_6$alkyl-, $C_1$-$C_6$ haloalkyl-, $C_1$-$C_6$alkoxy-$C_1$-$C_3$alkyl-, benzyl and phenyl, wherein the benzyl and phenyl groups are optionally substituted with one or more substituents selected from the group consisting of halogen, $C_1$-$C_6$alkyl-, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-;
$R^6$ is selected from the group consisting of hydrogen, $C_1$-$C_6$alkyl, $C_1$-$C_6$haloalkyl-, $C_1$-$C_6$alkoxy-$C_1$-$C_3$alkyl; and
p=0, 1 or 2.

Alkyl groups having a chain length of from 1 to 6 carbon atoms include, for example, methyl (Me, $CH_3$), ethyl (Et, $C_2H_5$), n-propyl (n-Pr), isopropyl (i-Pr), n-butyl (n-Bu), isobutyl (i-Bu), sec-butyl and tert-butyl (t-Bu).

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom may be joined to form a spiro group. Thus, the methyl groups present in two methoxy substituents may be joined to form a spiro 1,3 dioxolane substituent, for example. Such a possibility is within the scope of the present invention.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloro ethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-S(O)$_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino (e.g $NHR^5$) is, for example, methylamino, ethylamino, n-propylamino, isopropylamino or a butylamino isomer. Preference is given to alkylamino groups having a chain length of from 1 to 4 carbon atoms.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Cycloalkyl groups preferably have from 3 to 6 ring carbon atoms, for example cyclopropyl (c-propyl (c-Pr)), cyclobutyl (c-butyl (c-Bu)), cyclopentyl (c-pentyl) and cyclohexyl (c-hexyl) and may be substituted or unsubstituted.

Aryl includes, for example, phenyl and benzyl groups which may be optionally substituted in a mono- or polysubstituted form, in which case the substituents may, as desired, be in the ortho-, meta- and/or para-position(s).

In a particular aspect of the present invention there is provided a compound of Formula (I), wherein $A^1$ is CH and $A^2$ is N.

In another aspect of the present invention there is provided a compound of Formula (I), wherein $A^1$ is N and $A^2$ is CH.

Particularly preferred is wherein $A^1$ and $A^2$ are both N.

In a preferred embodiment, $R^1$ is selected from the group consisting of methyl, ethyl and propyl, preferably methyl.

In one particular aspect $R^2$ is selected from the group consisting of hydroxyl, chlorine, $C_1$-$C_6$alkoxy- (e.g ethoxy), $C_{1-6}$haloalkoxy-, $C_1$-$C_6$alkoxy-$C_1$-$C_3$alkoxy- and —$NHR^5$.

In another particular aspect, $R^2$ is selected from the group consisting of hydroxyl and —$NHR^5$.

In another particular aspect, $R^2$ is selected from the group consisting of —NHmethyl, NHn-butyl, —NHphenyl and hydroxyl.

In a particularly preferred embodiment, $R^2$ is chlorine.

In another embodiment $R^3$ is selected from the group consisting of hydrogen, halogen, $C_1$-$C_6$ alkyl (e.g methyl, ethyl, n-propyl, i-propyl, n-butyl, t-butyl), $C_1$-$C_6$ haloalkyl- (e.g —$CF_3$ or —$CH_2CF_3$), $C_1$-$C_6$alkoxy-$C_1$-$C_3$alkyl- (e.g ethoxymethyl-) and phenyl, wherein the phenyl is optionally substituted with one or more substituents selected from the group consisting of halogen, $C_1$-$C_6$ alkyl, cyano, nitro, $C_1$-$C_6$ haloalkyl-, $C_1$-$C_6$alkyl-S(O)p-, $C_1$-$C_6$alkoxy- and $C_1$-$C_6$haloalkoxy-.

In a preferred embodiment $R^3$ is methyl.

In another particularly preferred embodiment, $R^3$ is phenyl, optionally substituted with one or more (preferably one, two or three) substituents selected from the group consisting of halogen (preferably fluorine, chlorine or bromine, most preferably chlorine), $C_1$-$C_6$ alkyl (preferably methyl), cyano, nitro, $C_1$-$C_6$ haloalkyl- (preferably trifluoromethyl), $C_1$-$C_6$alkyl-S(O)p- (preferably —$S(O)_2Me$), $C_1$-$C_6$alkoxy- (preferably methoxy) and $C_1$-$C_6$haloalkoxy- (preferably trifluoromethoxy-).

In another embodiment $R^4$ is methyl.

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula (I) may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula (I) may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chloride, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fenquinotrione, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+mono linuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+tri-allate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Sixteenth Edition, British Crop Protection Council, 2012.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4).

Other possibilities include safener compounds disclosed in, for example, EP0365484 e.g N-(2-methoxybenzoyl)-4-[(methylaminocarbonyl)amino]benzenesulfonamide.

Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino]benzenesulfonamide.

The safeners of the compound of Formula I may also be in the form of esters or salts, as mentioned e.g. in The Pesticide Manual, 16$^{th}$ Edition (BCPC), 2012. The reference to cloquintocet-mexyl also applies to a lithium, sodium, potassium, calcium, magnesium, aluminium, iron, ammonium, quaternary ammonium, sulfonium or phosphonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rendering crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Cenchrus, Lolium, Festuca, Setaria, Eleusine, Sorghum* or *Avena* species. Several HPPD-tolerant soybean transgenic "events" are known, and include for example SYHT04R (WO2012/082542), SYHT0H2 (WO2012/082548) and FG72.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis, Alopecurus, Avena, Brachiaria, Bromus, Cenchrus, Cyperus, Digitaria, Echinochloa, Eleusine, Lolium, Monochoria, Rottboellia, Sagittaria, Scirpus, Setaria* and *Sorghum*, and dicotyledonous species, for example *Abutilon, Amaranthus, Ambrosia, Chenopodium, Chrysanthemum, Conyza, Galium, Ipomoea, Nasturtium, Sida, Sinapis, Solanum, Stellaria, Veronica, Viola* and *Xanthium*. The compounds of the present invention have been shown to exhibit particularly good activity against certain grass weed species, especially *Lolium Perenne*. Weeds can also include plants which may be considered crop plants but which are growing outside a crop area (escapes), or which grow from seed left over from a previous planting of a different crop (volunteers). Such volunteers or escapes may be tolerant to certain other herbicides.

The compounds of the present invention can be prepared according to the following schemes.

Scheme 1:- Reaction of an activated carboxylic acid with a 1-alkyl-5-aminotetrazole or an aminotriazole:

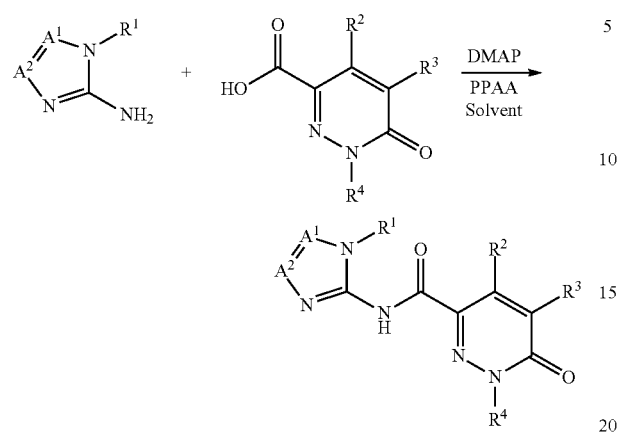

Scheme 2:- Reaction of an activated carboxylic acid with a 5-(alkylamino)tetrazole:

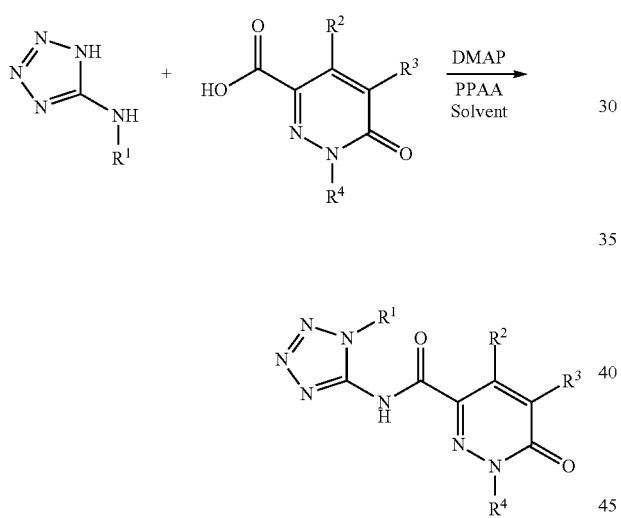

In each case, DMAP=4-(dimethylamino) pyridine, PPAA=1-propanephosphonic acid cyclic anhydride, the solvent is a non-protic organic solvent such as ethyl acetate, tetrahydofuran, 1,4-dioxane or dichloromethane, and the reaction may be subjected to heating by microwave irradiation.

Scheme 3: Reaction of an acid chloride with an aminotriazole or an aminotetrazole:

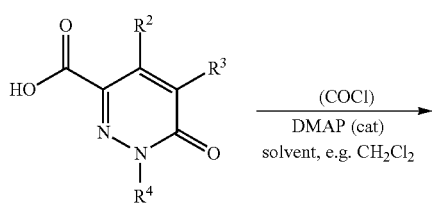

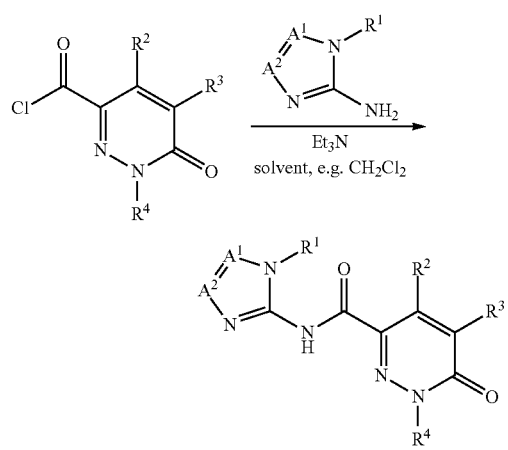

Scheme 4: Activation of an acid with N,N'-carbonyldiimidazole (CDI), and reaction with an aminotriazole or an aminotetrazole:

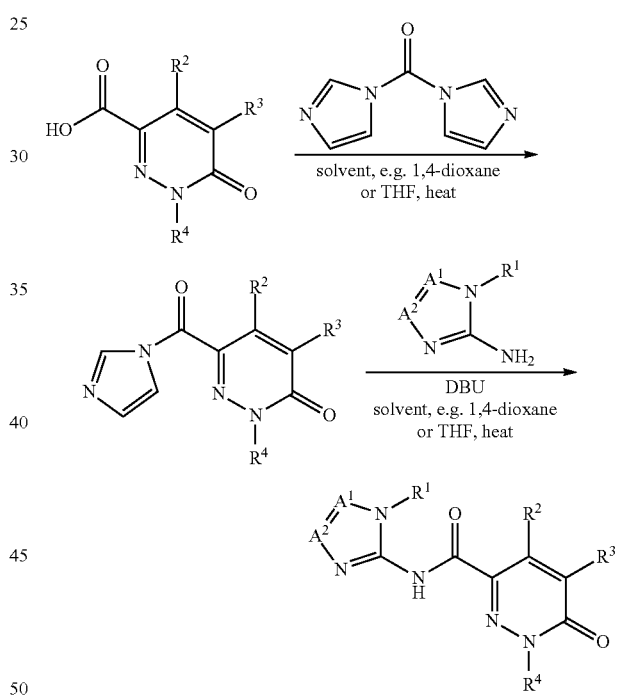

where THF=tetrahydrofuran and DBU=1,8-diazabicyclo[5.4.0]undec-7-ene

Scheme 5: Reaction of a carboxylic ester with an aminotriazole or an aminotetrazole:

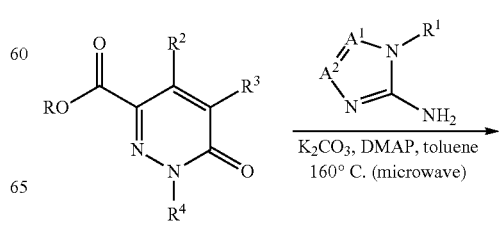

-continued
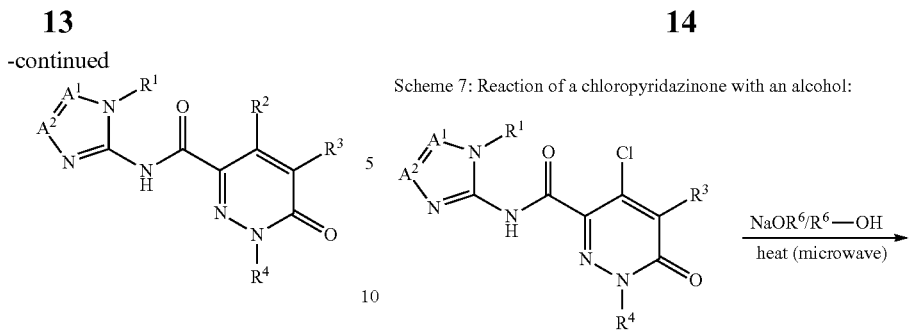
Scheme 6: Reaction of a chloropyridazinone with an amine:
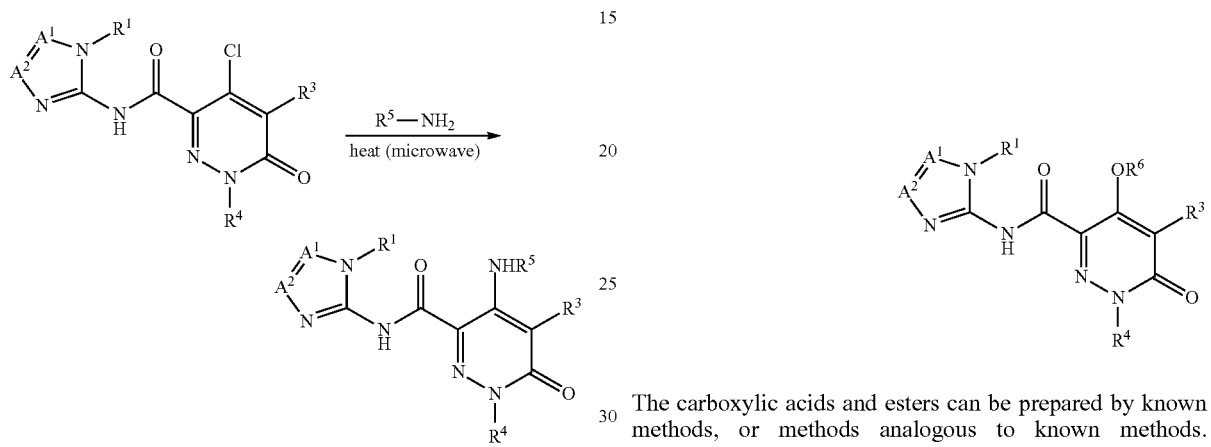
Scheme 7: Reaction of a chloropyridazinone with an alcohol:
The carboxylic acids and esters can be prepared by known methods, or methods analogous to known methods. Examples of such methods are given in Schemes 8 and 9, below.
Scheme 8:
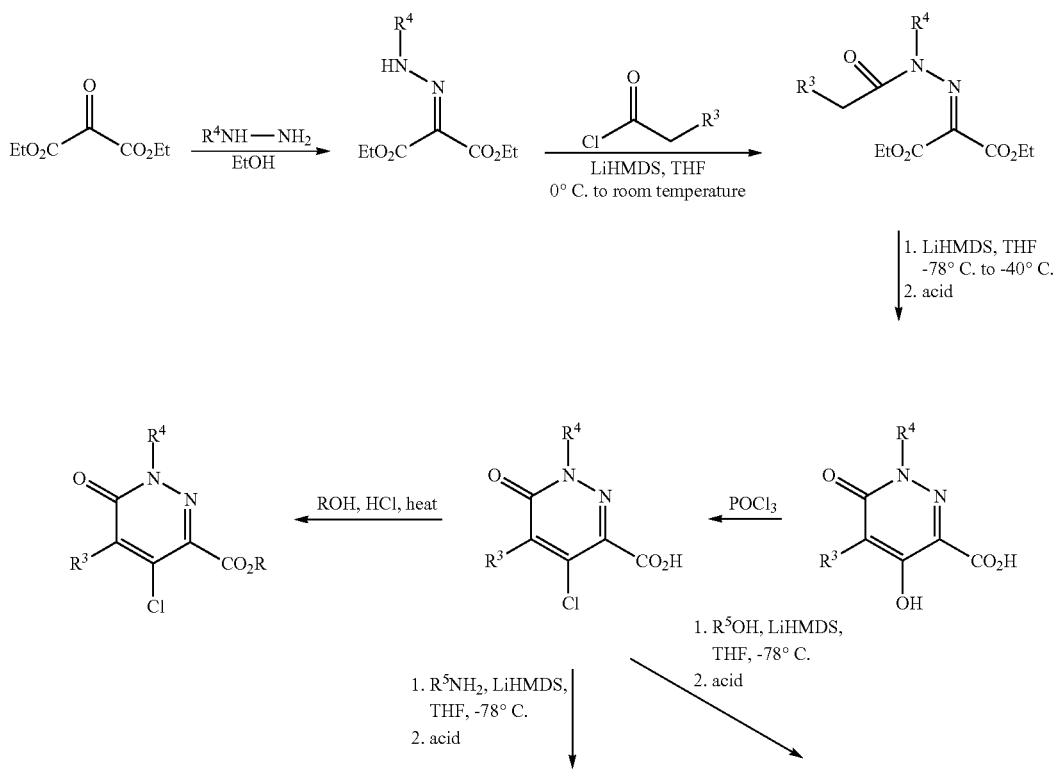

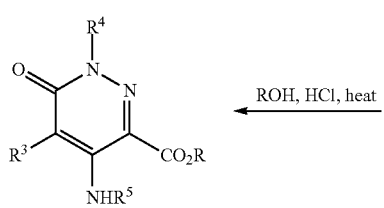
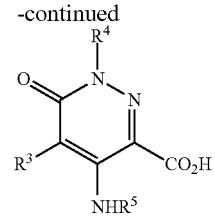
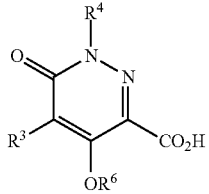
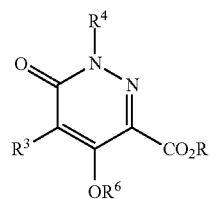

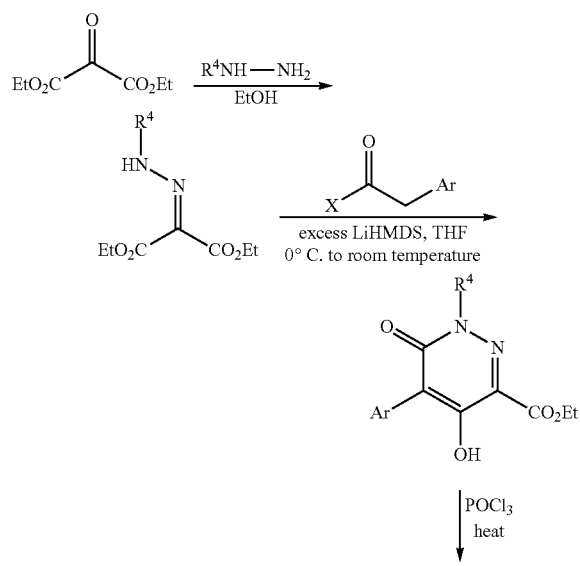

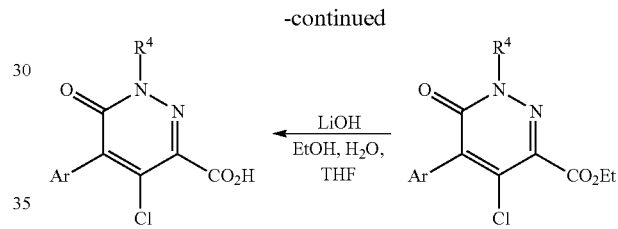

wherein EtOH is ethanol, THF is tetrahydrofuran, LiHMDS is lithium hexamethyl disilazide, acid is an aqueous inorganic acid such as dilute hydrochloric acid or dilute sulphuric acid, Ar is phenyl or substituted phenyl and X is a chlorine atom or an N-linked imidazole.

The following non-limiting examples provide specific synthesis methods for representative compounds of the present invention, as referred to in Table 1 below.

PREPARATIVE EXAMPLE 1: PREPARATION OF COMPOUND 1.007

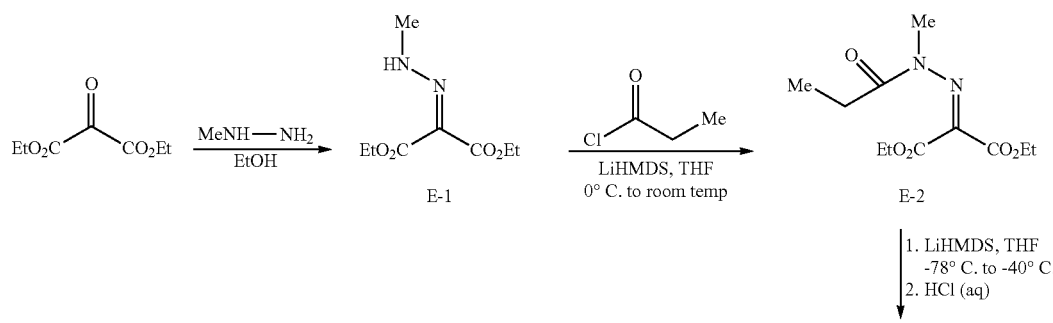

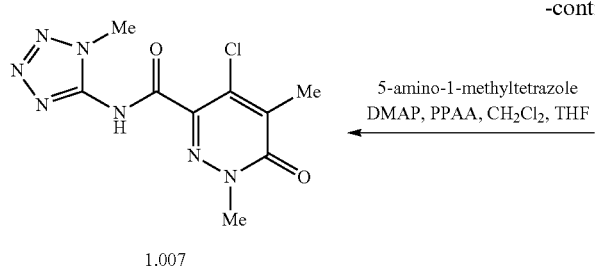

1.007

-continued

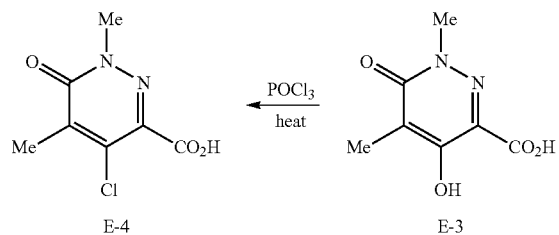

E-4    E-3

Step 1: Methyl hydrazine (58.2 gm, 66.5 mL, 1.26 mol) was added dropwise to a stirred solution of diethyl ketomalonate (200.0 g, 1.15 mol) in ethanol (1.2 L) at room temperature (during the addition temperature rose to 45° C.). The reaction mixture was then slowly heated to 60° C. and stirred at that temperature for 6 h. The mixture was then allowed to cool, and was stirred overnight at room temperature. The solvent was removed under reduced pressure, and the residue was diluted with ethyl acetate (ca. 500 mL). This was then washed with water (ca. 500 mL), and the aqueous washing was extracted with ethyl acetate (2×250 mL). The combined ethyl acetate layers were washed with brine (ca. 500 mL), dried over anhydrous sodium sulphate, and the solvent was removed under reduced pressure to leave the crude product as a thick orange gum. This was purified by column chromatography (100-200 mesh silica gel) using 10% ethyl acetate in hexanes as eluent to afford compound E-1 as a pale yellow oil (158.0 g).

1Hnmr (CDCl$_3$): 1.28-1.35 (6H, m); 3.38-3.40 (3H, d), 4.24-4.30 (4H, m); 11.31 (1H, br s)

Step 2: Lithium hexmethyldisilazide (LiHMDS; [1(M) solution in THF]; 314.5 ml, 314.5 mmol) was added dropwise to a stirred solution of compound E-1 (53.0 g, 262.1 mmol) in anhydrous tetrahydrofuran (THF; 530 mL) at 0° C. over 45 minutes (thick solid precipitate formed), and the mixture was stirred at 0° C. for 45 minutes. Propionylchloride (29.1 g, 314.5 mmol, 1.2 equiv) was then added dropwise at 0° C., and the clear brown-red solution thus obtained was allowed to warm to room temperature, then stirred overnight. The reaction mass was then cooled to 0° C. and carefully quenched with saturated aqueous ammonium chloride solution (ca. 50 mL) followed by water (ca. 100 mL). The solvents were removed under vacuum and the residue was diluted with ethyl acetate (ca. 300 mL) and washed with water (ca. 100 mL). The aqueous layer was washed with ethyl acetate (2×100 mL), and the combined ethyl acetate layers were washed with saturated aqueous sodium hydrogencarbonate solution (ca. 200 mL) and brine (2×200 mL). The organic layer was dried over anhydrous sodium sulphate and the solvent was removed under reduced pressure to afford crude compound E-2 (67 g,) as a dark brown oil which was used in the next step without further purification.

1Hnmr (CDCl$_3$): 1.38 (3H, t); 1.25-1.42 (6H, m); 2.84 (2H, q); 3.32 (3H, s); 4.24-4.40 (4H, m)

Step 3: A solution of compound E-2 (35.0 g, 135.5 mmol) in anhydrous tetrahydrofuran (THF; 50 mL) was added dropwise to a solution of lithium hexamethyl disilazide (LiHMDS) [1(M) in THF] (542 mL, 542 mmol) in anhydrous THF (650 mL) at −78° C. The brown reaction mixture was slowly allowed to warm to −40° C. and stirred for 1.5 hours, when it was cooled again to −78° C. and carefully quenched by the dropwise addition of water (500 mL). This mixture was then allowed to warm to room temperature and was stirred for 3 hours. The mixture was then concentrated under reduced pressure and the residual aqueous phase was cooled on ice bath and adjusted to pH ~1-2 by the slow addition of 6(N) aqueous hydrochloric acid. This mixture was stirred at room temperature for 2 days, when the solid precipitate that had formed was collected by filtration and washed with a little cold water. The solid was dried under reduced pressure, then triturated with 5% methanol in dichloromethane. The residual solid was filtered and dried to afford pure compound E-3 (10.5 g) as yellow solid.

1Hnmr (d6-DMSO): 1.91 (3H, s); 3.68 (3H, s)

Step 4: A suspension of compound E-3 (22.0 g, 119.5 mmol) in phosphorus oxychloride (POCl$_3$: 109 mL) was treated with diethyl aniline (1.9 mL, 0.1 equiv) and heated to 100° C. for 2.5 days. The dark solution was cooled to room temperature and the excess POCl$_3$ was removed under reduced pressure. The residue was carefully poured onto excess crushed ice with vigorous stirring. The black precipitate thus obtained was extracted four times with hot ethyl acetate, and the combined ethyl acetate extracts were filtered. The solution thus obtained was dried over anhydrous sodium sulphate, and the solvent was removed under reduced pressure to leave a dark brown solid. This was triturated with diethyl ether to afford pure compound E-4 (9.9 g) as a brown solid. A further crop (7.0 g) was obtained by extraction of the aqueous mixture from the crushed ice with ethyl acetate (3×100 mL).

1Hnmr (d6-DMSO): 2.20 (3H, s), 3.67 (3H, s)

Step 5: A stirred mixture of compound E-4 (214 mg, 1.0563 mmol) and 1-methyl-5-aminotetrazole (103 mg, 1.0394 mmol) in dichloromethane (10 mL) was treated with tetrahydrofuran (THF: 10 mL) to aid solubility, and then 4-(dimethyamino) pyridine (DMAP; 256 mg, 2.0745 mmol) was added. The resultant solution was stirred at room temperature for 1 hour, before the addition of 1-propanphosphonic acid cyclic anhydride (PPAA; 50 mass % in ethyl acetate; 1.34 mL, 2.11 mmol). The solution was then stirred for 5 h, and left to stand overnight. Water was then added and the mixture was stirred vigorously. The dichloromethane layer was separated, evaporated under reduced pressure and the residue was absorbed onto silica gel. This was separated by chromatography (CombiFlash Rf, eluting with 0-5% methanol in dichloromethane to afford compound 1.007 as an off-white solid (182 mg).

1 Hnmr (CDCl3): 2.38 (3H, s); 3.94 (3H, s), 4.11 (3H, s), 11.09 (1H, s)

PREPARATIVE EXAMPLE 2: PREPARATION OF COMPOUND 1.023

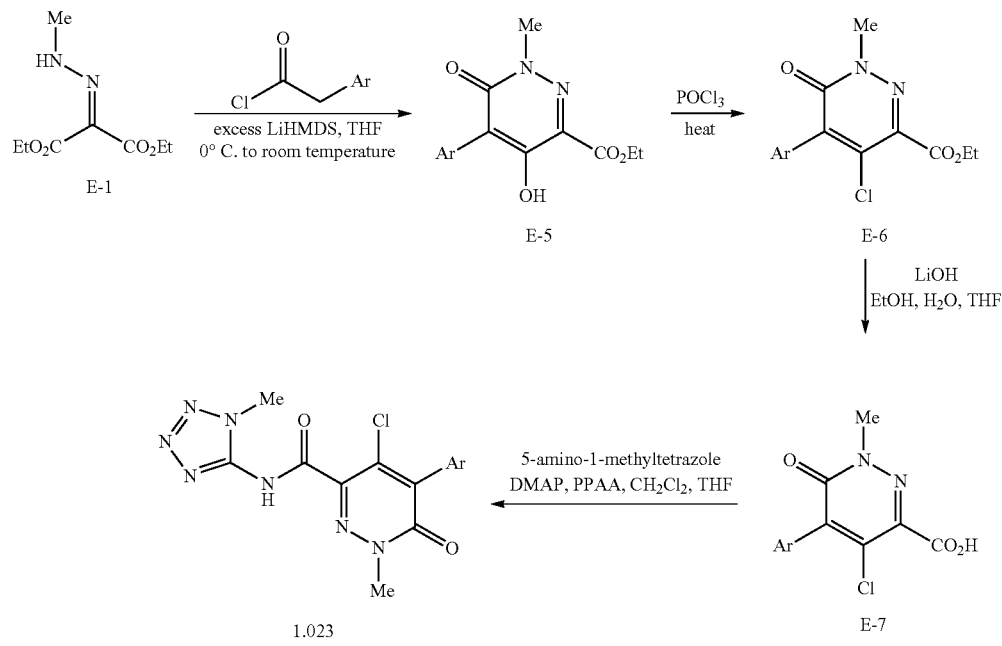

Ar = 4-CF$_3$-phenyl

Step 1: Oxalyl chloride (7.2 mmol, 7.2 mmol) was added dropwise to stirred solution of 4-(trifluoromethyl)phenylacetic acid (6 mmol, 6 mmol) in dichloromethane (20 mL), and 1 drop of dimethylformamide was added. The solution was stirred at room temperature for 2 hours and was then evaporated under reduced pressure to afford 4-(trifluoromethyl)phenylacetyl chloride, which was used directly without further purification. A solution of LiHMDS (1 mol/L in THF/ethylbenzene; 9 mmol) was added dropwise under nitrogen to a cooled (ice-water bath) stirred solution of compound E-1 (3 mmol, 3 mmol) in THF (10 mL). The resultant orange reaction mixture was stirred at 0° C. for 30 min, and then a solution of the acid chloride (prepared as described above) in THF (10 mL) was added dropwise. The reaction mixture was stirred at 0° C., and was then allowed to warm to room temperature and allowed to stand overnight. The mixture was then poured into water, and extracted with dichloromethane. The dichloromethane extracts were dried and evaporated to leave a viscous orange oil, which was separated by chromatography (CombiFlash Rf (40 g Gold column), eluting with 0-50% ethyl acetate in isohexane over 20 min) to afford crude compound E-5 as a viscous gum (250 mg), which was used in the next step without further purification.

1Hnmr (CDCl3): inter alia 1.49 (3H, t); 3.93 (3H, s); 4.55 (2H, q); 7.69 (2H, d); 7.76 (2H, d); 11.01 (1H, br s)

Step 2: A mixture of compound E-5 (250 mg, 0.3652 mmol) and phosphorus oxychloride (3 mL) was heated to 120° C. in a microwave oven for 40 mins, and was then allowed to cool and left to stand overnight. The mixture was then added, dropwise with vigorous stirring to ice-water, over a period of 10 min. Stirring was continued for a further 10 min, then the mixture was extracted with dichloromethane. The organic phase was dried (MgSO4), filtered and evaporated to produce a viscous dark brown oil, which was absorbed onto silica and separated by chromatography (CombiFlash Rf; eluting with 0-50% ethyl acetate in isohexane over 20 mins) to afford compound E-6 as a viscous yellow oil (60 mg).

1Hnmr (CDCl3): 1.43 (3H, t); 3.87 (3H, s); 4.47 (2H, q); 7.55 (2H, d); 7.73 (2H, d)

Step 3: a solution of lithium hydroxide monohydrate (15 mg, 0.3575 mmol) in water (2 mL) was added dropwise to a stirred solution of compound E-6 (45 mg, 0.1248 mmol) in 1,4-dioxane (5 mL). The mixture was stirred at room temperature for 2 hours, when LC-MS analysis showed the product peak for compound E-7 (MH+=333,335; 1×Cl) and no sign of unreacted ester. The mixture was then evaporated to produce an off white solid, which was used directly in the next step without further purification.

Step 4: A stirred solution of compound E-7 (50 mg, 0.1503 mmol) and 1-methyl-5-aminotetrazole (20 mg, 0.2018 mmol) in dichloromethane (10 mL) was treated with 4-(dimthylamino)pyridine (DMAP; 37 mg, 0.30286 mmol), and the mixture was stirred at room temperature for 1 hour. 1-Propanephosphonic acid cyclic anhydride (PPAA; 50 mass % in ethyl acetate; 0.5 mL, 0.8 mmol) was added and the mixture was stirred at room temperature for 10 mins. The mixture was then transferred into a microwave vial and heated to 120° C. in a microwave oven for 30 mins, when LC-MS analysis showed incomplete conversion. The mixture was returned to the microwave and was heated at 120° C. for 60 mins. The mixture was then allowed to cool and to stand at room temperature overnight. The mixture was then poured into water and was shaken vigorously. The organic phase was separated, concentrated under reduced pressure and then absorbed onto silica gel, and separated by chromatography (CombiFlash Rf (4g Gold Column), eluting with 0-10% methanol in dichloromethane over 20 mins) to afford compound 1.23 as an off-white solid (15 mg).

1Hnmr (CDCl3): 4.01 (3H, s), 4.13 (3H, s), 7.54 (2H, d), 7.77 (2H, d), 11.87 (1H, br s),

PREPARATIVE EXAMPLE 3: PREPARATION OF COMPOUND 1.037

Step 2: Compound E-8 was converted to compound E-9 using a method analogous to that described in Preparative Example 2, Step 2. Compound E-9 was obtained as a pale yellow oil.

1Hnmr (CDCl3): 1.43 (3H, t); 3.87 (3H, s); 4.46 (2H, q); 7.22 (1H, d); 7.59 (1H, t); 7.67 (1H, t); 7.81 (1H, d)

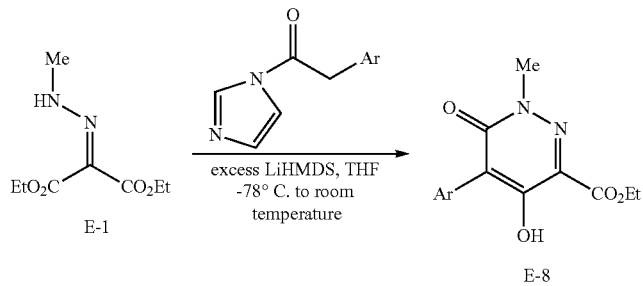

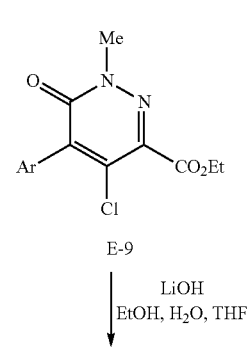

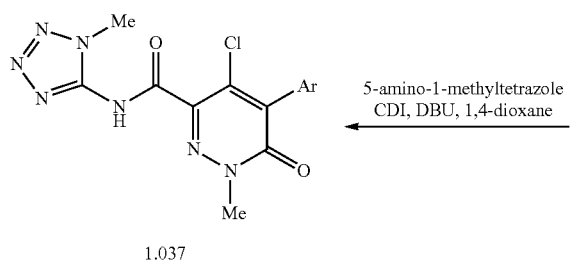

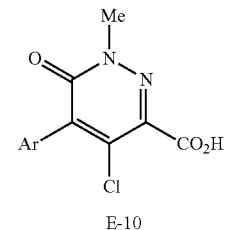

1.037

Ar = 2-CF3-phenyl

Step 1: Carbonyl diimidazole (0.51 g, 3.2 mmol) was added to a stirred solution of 2-(trifluoromethyl)phenylacetic acid (0.61 g, 3.0 mmol) in anhydrous tetrahydrofuran (6 mL) at room temperature The resulting mixture was stirred for 1 h, when LC-MS analysis showed that N-(2-(trifluoromethyl)phenylacetyl)-imidazole had formed.

A stirred solution of compound E-1 (0.61 g, 3.0 mmol) in anhydrous THF (6 mL) was cooled to 0° C. in an ice-bath, and treated dropwise over 15 minutes with a solution of LiHMDS in THF (1 mmol/L; 6.0 mL, 6.0 mmol) The resulting mixture was stirred at 0 C for a further 10 min, then the solution of N-acyl imidazole (prepared as described above) was then added dropwise at 0° C. over ca. 5 min. The resulting dark orange solution was stirred at 0° C. for 10 min, and was then allowed to warm to room temperature and stirred overnight. The mixture was then cooled to 0° C. and 2M HCl (ca. 10 mL) was added dropwise, forming a yellow solution. The organic phase was separated and the aqueous phase extracted with ethyl acetate. The combined organic phases were washed with brine, passed through a phase-separating cartridge, and the filtrate was then evaporated under reduced pressure. The residue was separated by chromatography (CombiFlash Rf, 12 g Gold column, eluting with 10-40% ethyl acetate in hexanes) to afford compound E-8 as a pale yellow solid (230 mg).

1Hnmr (CDCl3): 1.48 (3H, t); 3.91 (3H, s); 4.53 (2H, qd); 7.27 (1H, d); 7.54 (1H, t); 7.63 (1H, t); 7.79 (1H, d); 10.65 (1H, br s)

Step 3: Compound E-9 was converted to compound E-10 using a method analogous to that described in Preparative Example 2, Step 3. Compound E-10 was obtained as an off-white solid.

1Hnmr (CD3OD): 3.86 (3H, s); 7.38 (1H, d); 7.70 (1H, t); 7.78 (1H, t); 7.87 (1H, d)

Step 4: A stirred solution of compound E-10 (0.065 g, 0.1954 mmol) in anhydrous 1,4-dioxane (2 mL) was treated with N,N'-carbonyldiimidazole (0.03802 g, 0.2344 mmol) under a nitrogen atmosphere. The mixture was heated to 100° C. for 1 hour, then allowed to cool 5-amino-1-methyltetrazol-e (0.02323 g, 0.2344 mmol) was then added in one portion, followed by 1,8-diazabicyclo[5.4.0]undec-7-ene (DBU) (0.0304 g, 0.0298 mL, 0.1954 mmol), and the resulting mixture was reheated in a microwave oven to 100° C. and stirred at that temperature for 2 hours. The mixture was then cooled and evaporated under reduced pressure, and the residue was poured into 2M HCl and extracted with dichloromethane. The combined organic layers were washed with brine, passed through a phase-separating cartridge, and then the filtrate was evaporated under reduced pressure. The crude product was purified by flash chromatography (CombiFlash Rf, eluting with 0-3% methanol in dichloromethane,) to afford compound 1.037 as an off-white solid (57 mg).

1Hnmr (CD3OD): 3.90 (3H, s); 4.04 (3H, s); 7.37 (1H, d); 7.70 (1H, t); 7.78 (1H, t), 7.87 (1H, d)

PREPARATIVE EXAMPLE 4: PREPARATION OF COMPOUND 1.008

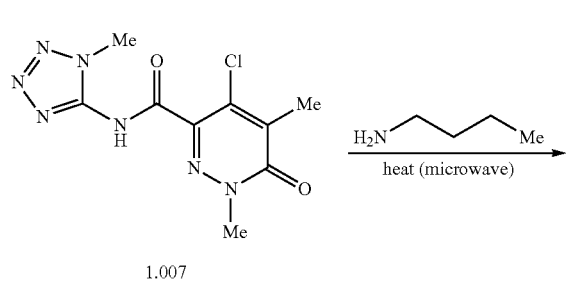

PREPARATIVE EXAMPLE 5: PREPARATION OF COMPOUND 1.009

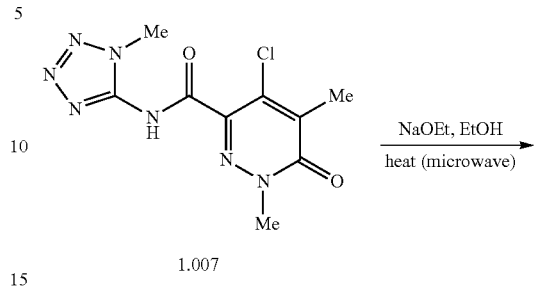

Step 1: A stirred mixture of compound 1.007 (188 mg, 0.6627 mmol) and n-butylamine (4 mL) was heated to 100° C. in a microwave oven for 30 mins. The mixture was then evaporated under reduced pressure (to remove excess butylamine) and the residue was chromatographed (Combi-Flash Rf, eluting with 0-5% methanol in dichloromethane over 30 mins) to afford the title compound as a pale yellow solid (41 mg).

1Hnmr (CDCl3): 0.95 (3H, t); 1.35-1.346 (2H, m), 1.54-1.63 (2H+H2O, m), 2.27 (3H, s), 3.46 (2H, q), 3.83 (3H, s), 4.07 (3H, s), 7.60 (1H, br t), 9.87 (1H, br s), Step 1: A stirred solution of compound 1.007 (141 mg, 0.497 mmol) in sodium ethoxide in ethanol (2 mL) was heated to 100° C. in a microwave oven for 30 mins. Water was then added and the mixture was extracted with ethyl acetate. The aqueous phase was evaporated under reduced pressure to leave an orange-brown solid, which was separated by chromatography (CombiFlash Rf, eluting with 0-5% methanol in dichloromethane, then up to 30% methanol over 35 mins) to afford the title compound (35 mg) as a white solid.

1 Hnmr (CDCl3): 1.47 (3H, t) 2.20 (3H, s), 3.90 (3H, s), 4.12-4.05 (5H, m),

PREPARATIVE EXAMPLE 6: PREPARATION OF COMPOUND 1.022

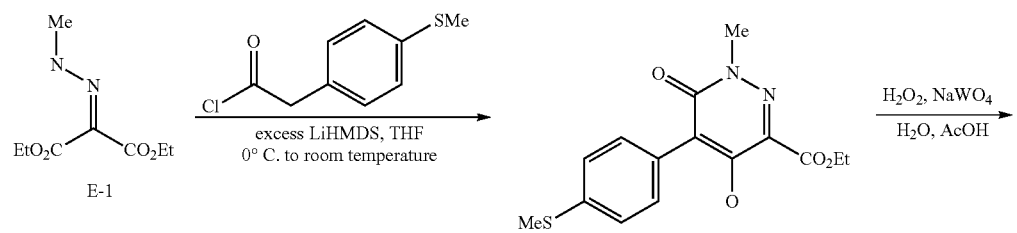

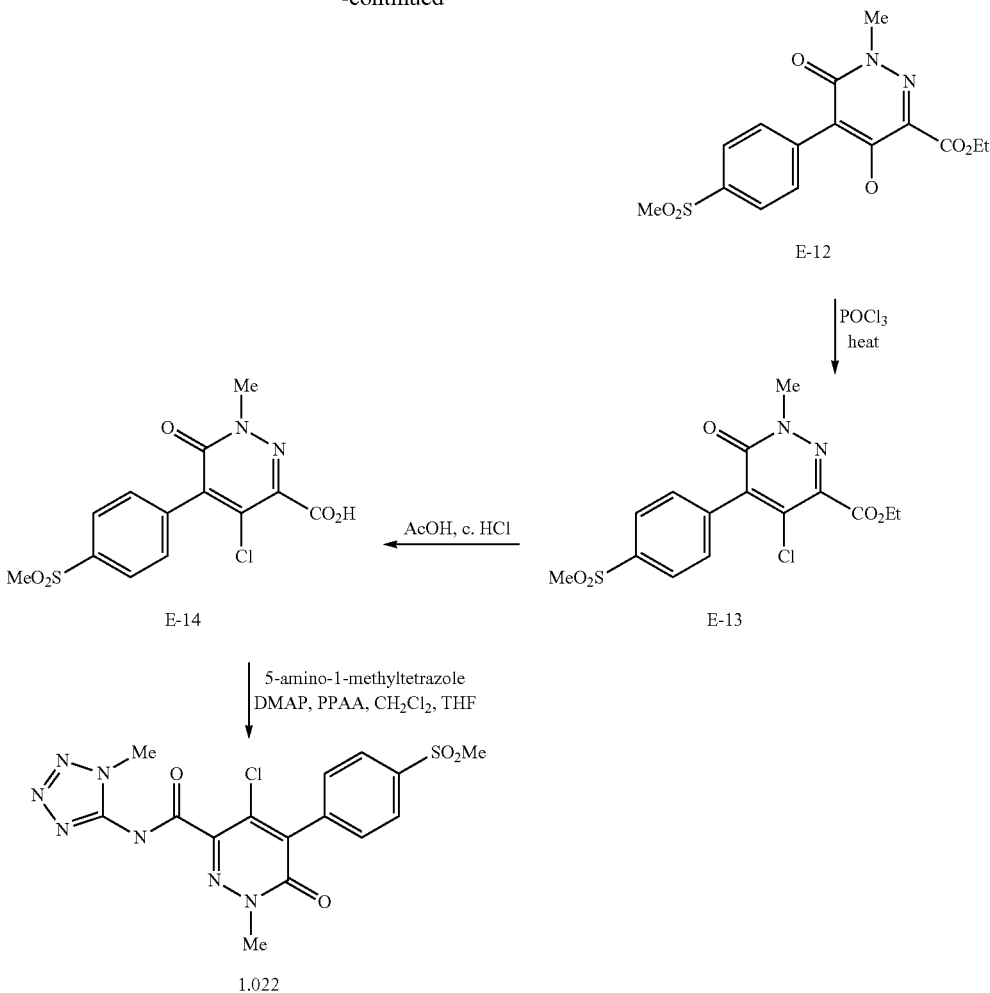

Step 1: Oxalyl chloride (0.84 mL, 9.6 mmol) was added dropwise to stirred solution of 4-methylsulfanyl-phenylacetic acid (1.5 g, 8.2 mmol) in dichloromethane (20 mL) containing one drop of dimethylformamide. The reaction mixture was stirred at room temperature for 4 hours, and was then evaporated under reduced pressure to afford crude 4-methylsulfanyl-phenylacetyl chloride, which was used without further purification. A stirred solution of compound E-1 (4 mmol) in tetrahydrofuran (10 mL) was cooled in an ice bath and treated dropwise with a solution of lithium hexamethyldisilazide (LHMDS; 1 mol/L in tetrahydrofuran/ethyl benzene; 12 mmol) under a nitrogen atmosphere, and the reaction mixture was then stirred with cooling for a further 30 mins. A solution of the crude 4-methylsulfanyl-phenylacetyl chloride (prepared as described above) in tetrahydrofuran (10 mL) was then added dropwise at 0° C., and the mixture was stirred at this temperature for a further 30 mins. The mixture was then allowed to warm to room temperature and stirring was continued overnight. The reaction mixture was then poured into water, acidified with 2M hydrochloric acid and extracted with dichloromethane. The dichloromethane extract was evaporated under reduced pressure to leave a viscous orange oil, which was separated by chromatography (CombiFlash Rf, eluting with 0-50% ethyl acetate/isohexane) to afford compound E-11 as a yellow solid (390 mg).

1H nmr (CDCl3): 1.48 (3H, t); 2.51 (3H, s); 3.92 (3H, s); 4.54 (2H, q); 7.31 (2H, d); 7.59 (2H, d); 10.87 (1H, s)

Step 2: A stirred mixture of compound E-11 (50 mg, 0.1561 mmol) and sodium tungstate dihydrate in acetic acid (5 ml) was treated dropwise with a solution of hydrogen peroxide (35% in water; 0.02 mL), and the mixture was stirred at room temperature for 3 hours. The reaction was quenched with aqueous sodium metabisulfite solution, and extracted into ethyl acetate. The ethyl acetate extracts were evaporated to dryness under reduced pressure (using toluene to remove water and acetic acid) to leave a yellow gum. This was separated by chromatography (CombiFlash Rf, eluting with 0-60% ethyl acetate/isohexane) to afford compound E-12 as a yellow gum (31 mg).

1Hnmr (CD3OD): 1.44 (3H, t); 3.15 (3H, s); 3.87 (3H, s); 4.51 (2H, q); 7.82 (2H, d); 8.00 (2H, d)

Step 3: Compound E-12 was converted to compound E-13 using a method analogous to that described in Preparative Example 2, Step 2.

1H nmr (CDCl3/CD3OD): 1.43 (3H, t); 3.12 (3H, s); 3.88 (3H, s); 4.45 (2H, q); 7.63 (2H, d); 8.06 (2H, d)

Step 4: A stirred solution of compound E-13 (120 mg, 0.3236 mmol) in acetic acid (5 mL) was treated with c. hydrochloric acid (1.0 mL). The reaction mixture was heated to 70° C. for 6 hours, then cooled and allowed to stand overnight. The mixture was heated again to 70° C. for 7 hours, then cooled and allowed to stand for 3 days. The mixture was evaporated to dryness under reduced pressure to leave crude compound E-14 as a solid. This was used in the next step without further purification.

1H nmr (CD3OD): 3.18 (3H, s); 3.79 (3H, s); 7.68 (2H, d); 8.05 (2H, d)

Step 5: Compound E-14 was converted to compound 1.022 using a method analogous to that described in Preparative Example 2, Step 4.

1H nmr (CDCl3): 3.11 (3H, s); 4.00 (3H, s); 4.12 (3H, s); 7.61 (2H, d); 8.08 (2H, s); 11.73 (1H, br s)

TABLE 1

Examples of herbicidal compounds of the present invention.

| Compound Number | Structure | 1H-NMR |
|---|---|---|
| 1.001 | 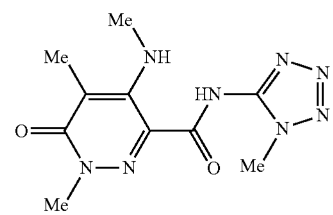 [SMILES: CNc1c(C(=O)Nc2nnnn2C)nn(C)c(=O)c1C] | |
| 1.002 | 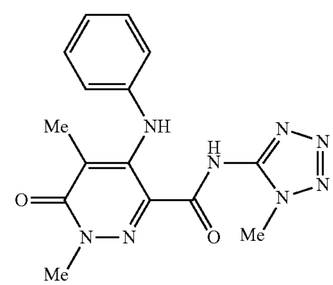 [SMILES: Cc1c(Nc2ccccc2)c(C(=O)Nc2nnnn2C)nn(C)c1=O] | |
| 1.003 | 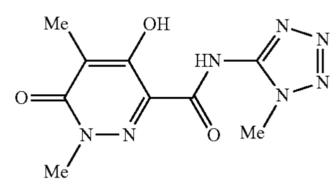 | |
| 1.004 | 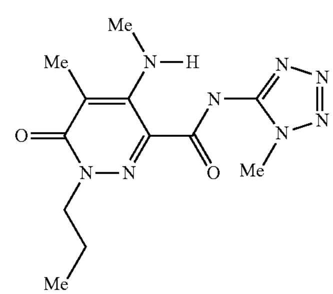 [SMILES: CCCn1nc(C(=O)Nc2nnnn2C)c(NC)c(C)c1=O] | |
| 1.005 | 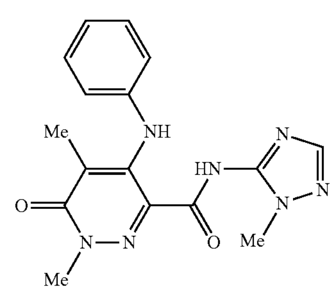 [SMILES: Cc1c(Nc2ccccc2)c(C(=O)Nc2ncnn2C)nn(C)c1=O] | |

TABLE 1-continued

Examples of herbicidal compounds of the present invention.

| Compound Number | Structure | 1H-NMR |
|---|---|---|
| 1.006 | [structure] | |
| 1.007 | [structure] | (CDCl$_3$): 1.28-1.35 (6H, m); 3.38-3.40 (3H, d), 4.24-4.30 (4H, m); 11.31 (1H, br s) |
| 1.008 | [structure] | (CDCl3): 0.95 (3H, t); 1.35-1.346 (2H, m), 1.54-1.63 (2H + H2O, m), 2.27 (3H, s), 3.46 (2H, q), 3.83 (3H, s), 4.07 (3H, s), 7.60 (1H, br t), 9.87 (1H, br s) |
| 1.009 | [structure] | (CDCl3): 1.47 (3H, t), 2.20 (3H, s), 3.90 (3H, s), 4.12-4.05 (5H, m) |
| 1.010 | [structure] | (d6-DMSO): 3.79 (3H, s); 3.96 (3H, s); 7.54-7.38 (5H, m); 11.88 (1H, br s) |
| 1.011 | [structure] | (d3-MeCN): 3.88 (3H, s); 3.98 (3H, s); 7.31 (1H, d); 7.53 (1H, dd); 7.70 (1H, d); 9.70 (1H, br s) |

TABLE 1-continued

Examples of herbicidal compounds of the present invention.

| Compound Number | Structure | 1H-NMR |
|---|---|---|
| 1.012 | 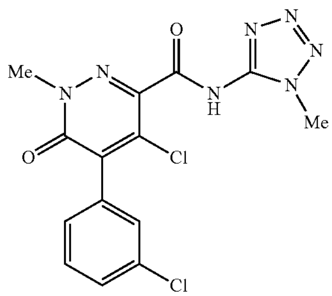 [SMILES: Cn1nnnc1NC(=O)c1nn(C)c(=O)c(-c2cccc(Cl)c2)c1Cl] | (d3-MeCN): 3.85 (3H, s); 3.98 (3H, s); 7.35 (1H, m); 7.41 (1H, s); 7.48-7.53 (2H, m) |
| 1.013 | 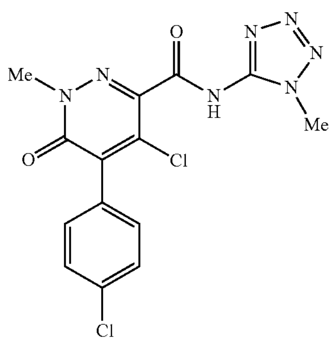 [SMILES: Cn1nnnc1NC(=O)c1nn(C)c(=O)c(-c2ccc(Cl)cc2)c1Cl] | (d3-MeCN): 3.86 (3H, s); 3.99 (3H, s); 7.40 (2H, d), 7.56 (2H, d); 9.76 (1H, br s) |
| 1.014 | 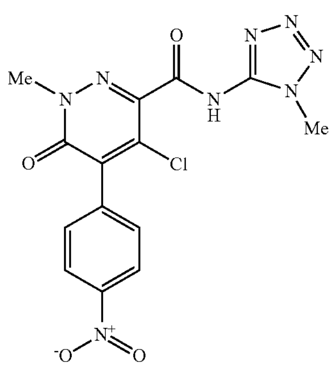 | (d3-MeCN): 3.88 (3H, s); 3.99 (3H, s); 7.65 (2H, d); 8.35 (2H, d); 9.80 (1H, br s) |
| 1.015 | 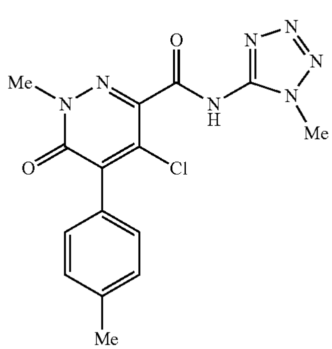 [SMILES: Cc1ccc(-c2c(Cl)c(C(=O)Nc3nnnn3C)nn(C)c2=O)cc1] | (d3-MeCN): 2.43 (3H, s); 3.85 (3H, s); 3.98 (3H, s); 7.27-7.32 (2H, m); 7.32-7.37 (2H, m); 9.77 (1H, br s) |

TABLE 1-continued

Examples of herbicidal compounds of the present invention.

| Compound Number | Structure | 1H-NMR |
|---|---|---|
| 1.016 | 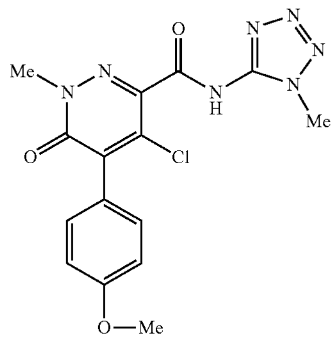 [SMILES: COc1ccc(-c2c(Cl)c(C(=O)Nc3nnnn3C)nn(C)c2=O)cc1] | (d3-MeCN): 3.84 (3H, s); 3.88 (3H, s); 3.98 (3H, s); 7.06 (2H, d); 7.39 (2H, d); 9.75 (1H, br s) |
| 1.017 | 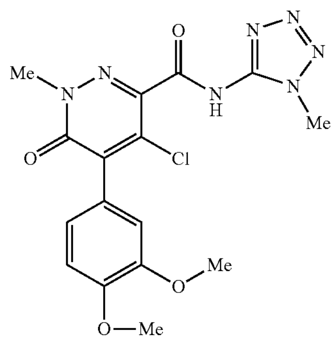 [SMILES: COc1ccc(-c2c(Cl)c(C(=O)Nc3nnnn3C)nn(C)c2=O)cc1OC] | (CD3OD): 3.84 (3H, s); 3.88 (3H, s); 3.89 (3H, s); 4.04 (3H, s) 7.01-7.09 (3H, m) |
| 1.018 | 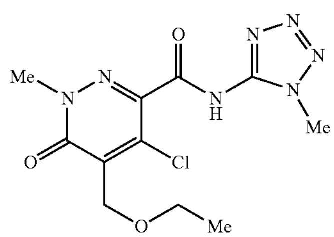 [SMILES: CCOCc1c(Cl)c(C(=O)Nc2nnnn2C)nn(C)c1=O] | |
| 1.019 | 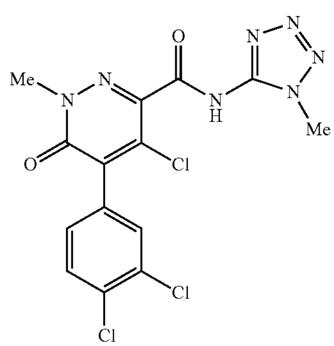 [SMILES: Cn1nnnc1NC(=O)c1nn(C)c(=O)c(-c2ccc(Cl)c(Cl)c2)c1Cl] | (d3-MeCN): 3.86 (3H, s); 3.98 (3H, s); 7.36 (1H, dd); 7.59 (1H, d); 7.69 (1H, d); 9.77 (1H, br s) |
| 1.020 | 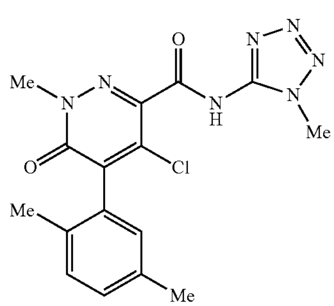 [SMILES: Cc1ccc(C)c(-c2c(Cl)c(C(=O)Nc3nnnn3C)nn(C)c2=O)c1] | (CD3OD): 2.10 (3H, s); 2.33 (3H, s); 3.90 (3H, s); 4.04 (3H, s); 6.94 (1H, s); 7.17 (1H, br dd); 7.22 (1H, d) |

TABLE 1-continued

Examples of herbicidal compounds of the present invention.

| Compound Number | Structure | 1H-NMR |
|---|---|---|
| 1.021 | 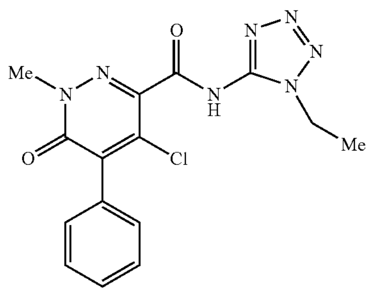 [SMILES: CCn1nnnc1NC(=O)c1nn(C)c(=O)c(-c2ccccc2)c1Cl] | |
| 1.022 | 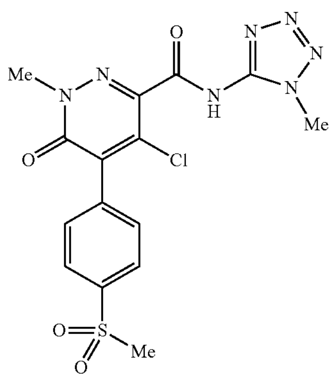 [SMILES: Cn1nnnc1NC(=O)c1nn(C)c(=O)c(-c2ccc(S(C)(=O)=O)cc2)c1Cl] | 1H nmr (CDCl3): 3.11 (3H, s); 4.00 (3H, s); 4.12 (3H, s); 7.61 (2H, d); 8.08 (2H, s); 11.73 (1H, br s) |
| 1.023 | 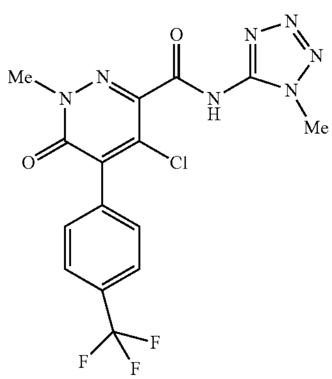 [SMILES: Cn1nnnc1NC(=O)c1nn(C)c(=O)c(-c2ccc(C(F)(F)F)cc2)c1Cl] | (CDCl3): 4.01 (3H, s), 4.13 (3H, s), 7.54 (2H, d), 7.77 (2H, d), 11.87 (1H, br s) |
| 1.024 | 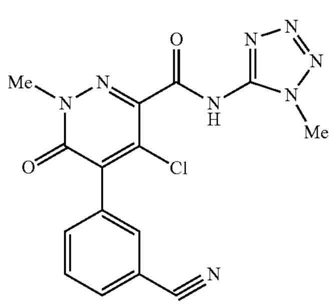 [SMILES: Cn1nnnc1NC(=O)c1nn(C)c(=O)c(-c2cccc(C#N)c2)c1Cl] | (d6-DMSO): 3.81 (3H, s); 3.96 (3H; s); 7.74 (2H, dd); 7.92 (1H, s); 7.97 (1H, d); 11.91 (1H, br s) |

TABLE 1-continued

Examples of herbicidal compounds of the present invention.

| Compound Number | Structure | 1H-NMR |
|---|---|---|
| 1.025 | 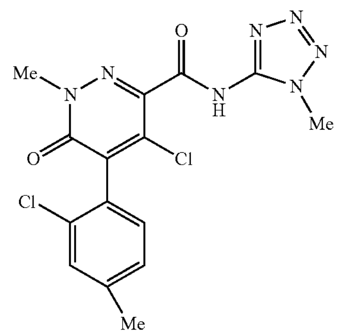 [SMILES: Cc1ccc(-c2c(Cl)c(C(=O)Nc3nnnn3C)nn(C)c2=O)c(Cl)c1] | (d6-DMSO): 2.37 (3H, s); 3.81 (3H, s); 3.96 (3H, s); 7.24-7.31 (2H, m); 7.46 (1H, s); 11.92 (1H, br s) |
| 1.026 | 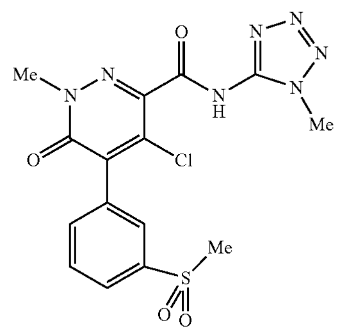 [SMILES: Cn1nnnc1NC(=O)c1nn(C)c(=O)c(-c2cccc(S(C)(=O)=O)c2)c1Cl] | (d6-DMSO): 3.37 (3H, s); 3.80 (3H, s); 3.96 (3H, s); 7.80-7.82 (2H, m); 7.99 (1H, s); 8.04 (1H, d); 11.89 (1H, br s) |
| 1.027 | 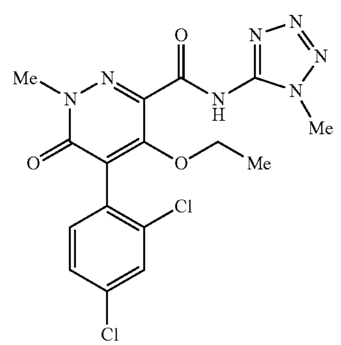 [SMILES: CCOc1c(C(=O)Nc2nnnn2C)nn(C)c(=O)c1-c1ccc(Cl)cc1Cl] | (d6-DMSO): 3.80 (3H, s); 3.94 (3H, s); 7.42 (1H, d); 7.59 (1H, dd); 7.82 (1H, d); 1.89 (1H, br s) |
| 1.028 | 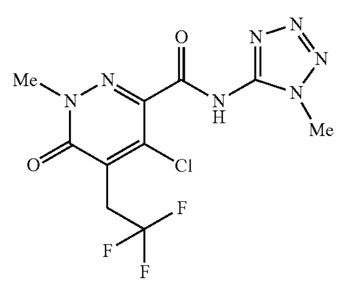 [SMILES: Cn1nnnc1NC(=O)c1nn(C)c(=O)c(CC(F)(F)F)c1Cl] | |
| 1.029 | 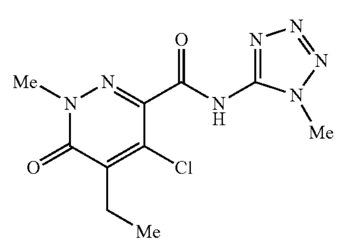 [SMILES: CCc1c(Cl)c(C(=O)Nc2nnnn2C)nn(C)c1=O] | (d6-DMSO): 1.09 (3H, t); 2.71 (2H, q); 3.75 (3H, s); 3.95 (3H, s); 11.81 (1H, br s) |

TABLE 1-continued

Examples of herbicidal compounds of the present invention.

| Compound Number | Structure | 1H-NMR |
|---|---|---|
| 1.030 | 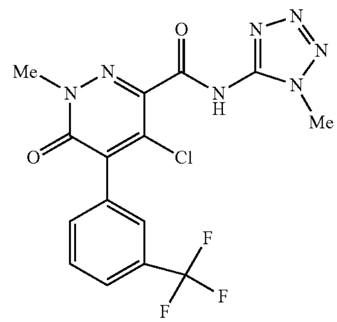 [SMILES: Cn1nnnc1NC(=O)c1nn(C)c(=O)c(-c2cccc(C(F)(F)F)c2)c1Cl] | (d3-MeCN): 3.89 (3H, s); 4.00 (3H, s); 7.65-7.77 (3H, m); 7.79-7.84 (1H, m); 9.70 (1H, br s) |
| 1.031 | 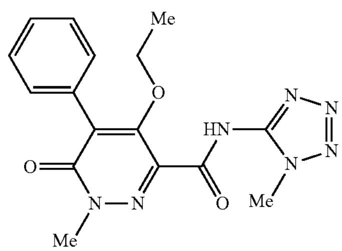 [SMILES: CCOc1c(C(=O)Nc2nnnn2C)nn(C)c(=O)c1-c1ccccc1] | (CDCl3): 1.14 (3H, t); 3.72 (2H, q); 3.95 (3H, s); 4.12 (3H, s); 7.39-7.49 (3H, m), 7.55 (2H, d); 10.9 (1H, br s) |
| 1.032 | 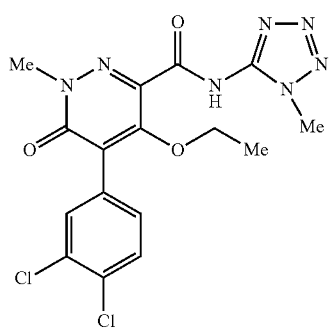 [SMILES: CCOc1c(C(=O)Nc2nnnn2C)nn(C)c(=O)c1-c1ccc(Cl)c(Cl)c1] | (d3-MeCN): 1.10 (3H, t); 3.82 (2H, q); 3.85 (3H, s); 3.98 (3H, s) 7.48 (1H, dd); 7.64 (1H, d) 7.71 (1H, d); 9.68 (1H, br s) |
| 1.033 | 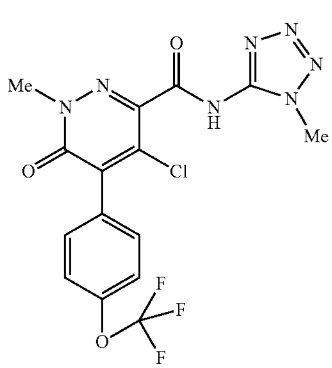 [SMILES: Cn1nnnc1NC(=O)c1nn(C)c(=O)c(-c2ccc(OC(F)(F)F)cc2)c1Cl] | (d6-DMSO): 3.80 (3H, s); 3.96 (3H, s); 7.51-7.58 (4H, m); 11.90 (1H, br s) |

TABLE 1-continued

Examples of herbicidal compounds of the present invention.

| Compound Number | Structure | 1H-NMR |
|---|---|---|
| 1.034 | (structure) | (d6-DMSO): 3.78 (3H, s); 3.96 (3H, s); 4.84 (2H, q); 7.17 (2H, d); 7.42 (2H, s); 11.88 (1H, br s) |
| 1.035 | (structure) | |
| 1.036 | (structure) | (d3-MeCN): 3.83 (3H, s); 3.85 (3H, s); 3.98 (3H, s); 6.73-6.98 (2H, m); 7.02-7.24 (1H, m) 7.44 (1H, t); 10.48 (1H, br s) |
| 1.037 | (structure) | (CD3OD): 3.90 (3H, s); 4.04 (3H, s); 7.37 (1H, d); 7.70 (1H, t); 7.78 (1H, t), 7.87 (1H, d) |
| 1.038 | (structure) | (d6-DMSO): 3.78 (3H, s); 3.96 (3H, s); 7.38 (2H, br m); 7.71 (2H, br m); 11.88 (1H, br s) |

TABLE 1-continued

Examples of herbicidal compounds of the present invention.

| Compound Number | Structure | 1H-NMR |
|---|---|---|
| 1.039 | 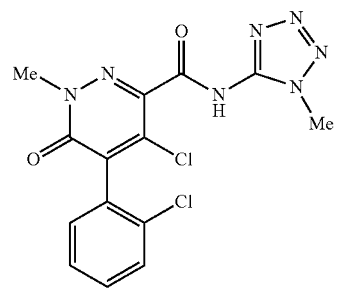 [SMILES: Cn1nnnc1NC(=O)c1nn(C)c(=O)c(-c2ccccc2Cl)c1Cl] | (d6-DMSO): inter alia 3.86 (3H, s); 3.99 (3H, s); 7.33 (1H, m); 7.40 (1H, m); 7.51 (1H, m); 7.64 (1H, d); 11.94 (1H, br s) |
| 1.040 | 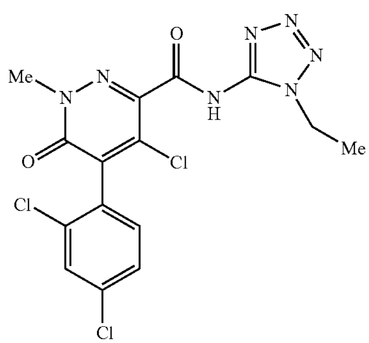 [SMILES: CCn1nnnc1NC(=O)c1nn(C)c(=O)c(-c2ccc(Cl)cc2Cl)c1Cl] | |
| 1.041 | 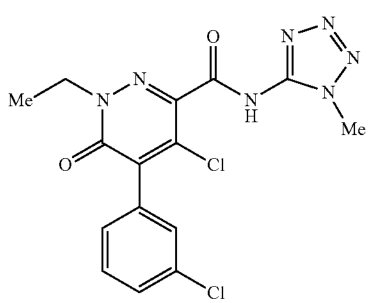 [SMILES: CCn1nc(C(=O)Nc2nnnn2C)c(Cl)c(-c2cccc(Cl)c2)c1=O] | |
| 1.042 | 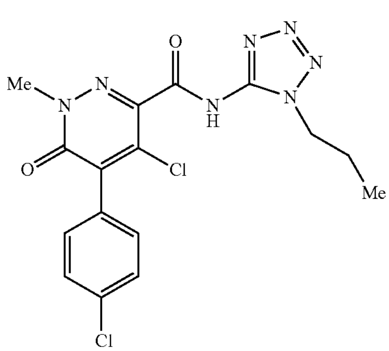 [SMILES: CCCn1nnnc1NC(=O)c1nn(C)c(=O)c(-c2ccc(Cl)cc2)c1Cl] | |

TABLE 1-continued

Examples of herbicidal compounds of the present invention.

| Compound Number | Structure | 1H-NMR |
|---|---|---|
| 1.043 | 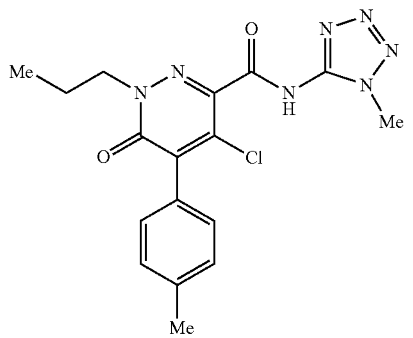 [SMILES: CCCn1nc(C(=O)Nc2nnnn2C)c(Cl)c(-c2ccc(C)cc2)c1=O] | |
| 1.044 | 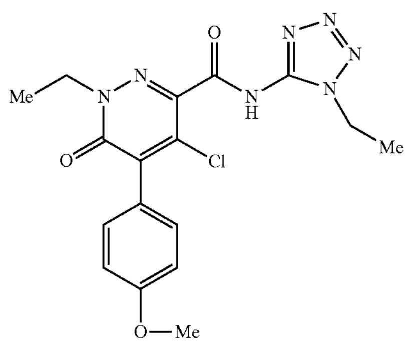 [SMILES: CCn1nnnc1NC(=O)c1nn(CC)c(=O)c(-c2ccc(OC)cc2)c1Cl] | |
| 1.045 | 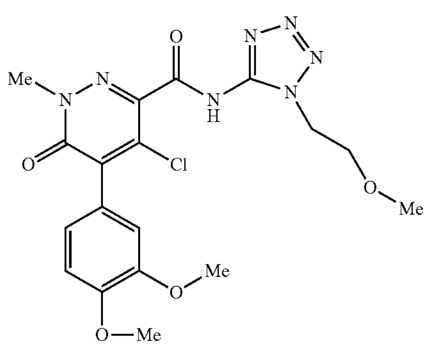 [SMILES: COCCn1nnnc1NC(=O)c1nn(C)c(=O)c(-c2ccc(OC)c(OC)c2)c1Cl] | |
| 1.046 | 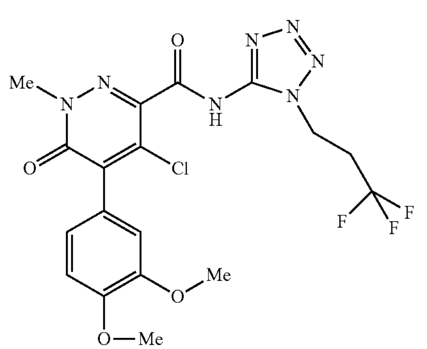 [SMILES: COc1ccc(-c2c(Cl)c(C(=O)Nc3nnnn3CCC(F)(F)F)nn(C)c2=O)cc1OC] | |

TABLE 1-continued

Examples of herbicidal compounds of the present invention.

| Compound Number | Structure | 1H-NMR |
|---|---|---|
| 1.047 | 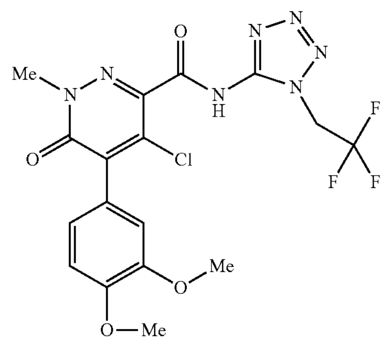 [SMILES: COc1ccc(-c2c(Cl)c(C(=O)Nc3nnnn3CC(F)(F)F)nn(C)c2=O)cc1OC] | |
| 1.048 | 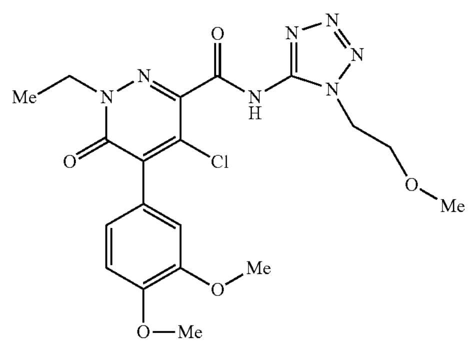 [SMILES: CCn1nc(C(=O)Nc2nnnn2CCOC)c(Cl)c(-c2ccc(OC)c(OC)c2)c1=O] | |
| 1.049 | 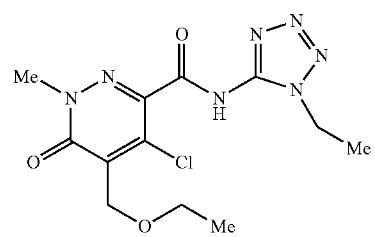 [SMILES: CCOCc1c(Cl)c(C(=O)Nc2nnnn2CC)nn(C)c1=O] | |
| 1.050 | 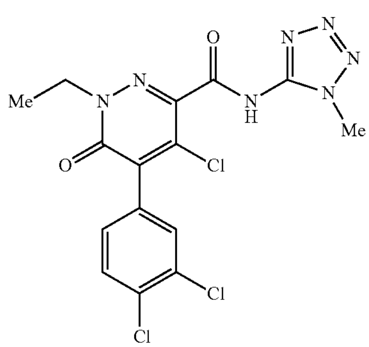 [SMILES: CCn1nc(C(=O)Nc2nnnn2C)c(Cl)c(-c2ccc(Cl)c(Cl)c2)c1=O] | |
| 1.051 | 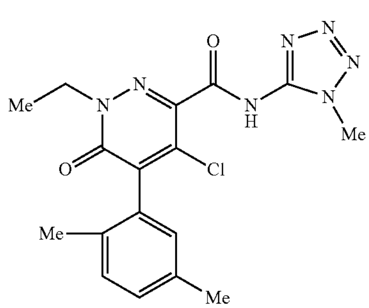 [SMILES: CCn1nc(C(=O)Nc2nnnn2C)c(Cl)c(-c2cc(C)ccc2C)c1=O] | |

TABLE 1-continued

Examples of herbicidal compounds of the present invention.

| Compound Number | Structure | 1H-NMR |
|---|---|---|
| 1.052 | 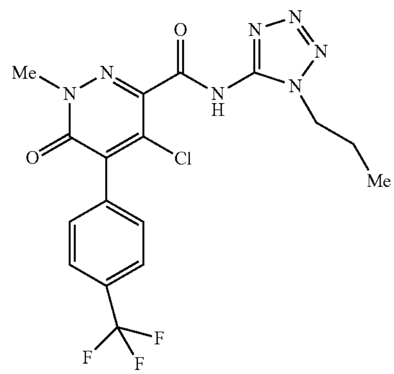 [SMILES: CCCn1nnnc1NC(=O)c1nn(C)c(=O)c(-c2ccc(C(F)(F)F)cc2)c1Cl] | |
| 1.053 | 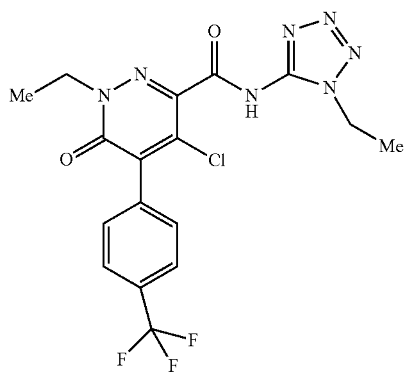 [SMILES: CCn1nnnc1NC(=O)c1nn(CC)c(=O)c(-c2ccc(C(F)(F)F)cc2)c1Cl] | |
| 1.054 | 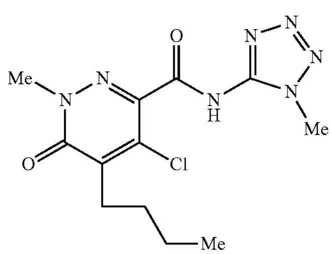 [SMILES: CCCCc1c(Cl)c(C(=O)Nc2nnnn2C)nn(C)c1=O] | |
| 1.055 | 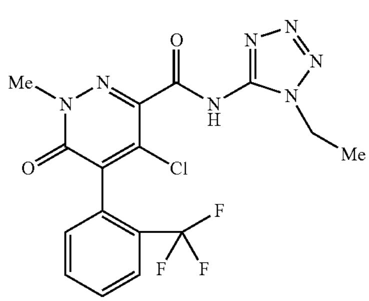 [SMILES: CCn1nnnc1NC(=O)c1nn(C)c(=O)c(-c2ccccc2C(F)(F)F)c1Cl] | |

TABLE 1-continued

Examples of herbicidal compounds of the present invention.

| Compound Number | Structure | 1H-NMR |
|---|---|---|
| 1.056 | 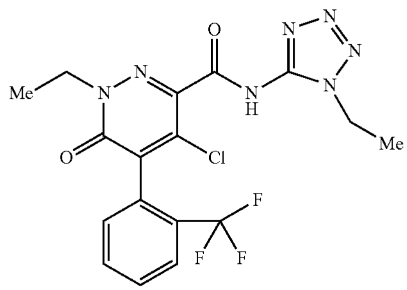 [SMILES: CCn1nnnc1NC(=O)c1nn(CC)c(=O)c(-c2ccccc2C(F)(F)F)c1Cl] | |
| 1.057 | 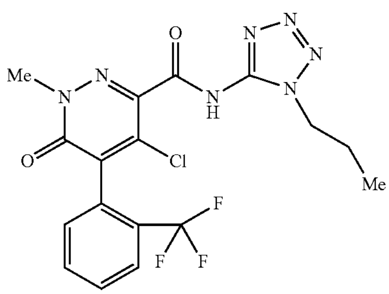 [SMILES: CCCn1nnnc1NC(=O)c1nn(C)c(=O)c(-c2ccccc2C(F)(F)F)c1Cl] | |
| 1.058 | 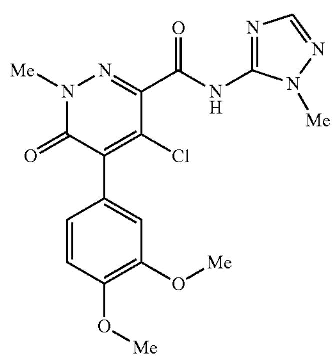 [SMILES: COc1ccc(-c2c(Cl)c(C(=O)Nc3ncnn3C)nn(C)c2=O)cc1OC] | |
| 1.059 | 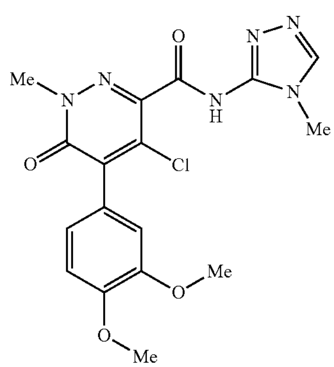 [SMILES: COc1ccc(-c2c(Cl)c(C(=O)Nc3nncn3C)nn(C)c2=O)cc1OC] | |

TABLE 1-continued

Examples of herbicidal compounds of the present invention.

| Compound Number | Structure | 1H-NMR |
|---|---|---|
| 1.060 | 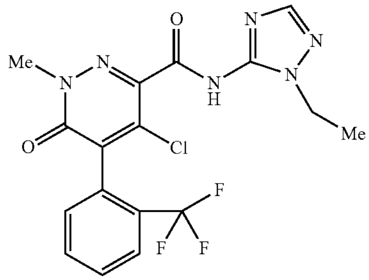 [SMILES: CCn1ncnc1NC(=O)c1nn(C)c(=O)c(-c2ccccc2C(F)(F)F)c1Cl] | |
| 1.061 | 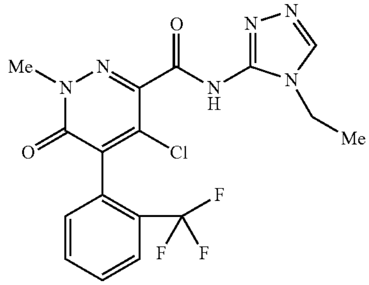 [SMILES: CCn1cnnc1NC(=O)c1nn(C)c(=O)c(-c2ccccc2C(F)(F)F)c1Cl] | |

BIOLOGICAL EXAMPLES

Seeds of a variety of test species are sown in standard soil in pots (*Lolium perenne* (LOLPE), *Solanum nigrum* (SOLNI), *Amaranthus retoflexus* (AMARE), *Setaria faberi* (SETFA), *Echinochloa crus-galli* (ECHCG), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds are applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

TABLE B1

| | POST Application | | | | | | PRE Application | | | | | |
|---|---|---|---|---|---|---|---|---|---|---|---|---|
| Compound | LOLPE | SOLNI | AMARE | SETFA | ECHCG | IPOHE | LOLPE | SOLNI | AMARE | SETFA | ECHCG | IPOHE |
| 1.007 | 5 | 5 | 5 | 5 | 5 | 5 | 5 | 5 | 5 | 5 | 5 | 5 |
| 1.008 | 1 | 5 | 5 | 1 | 1 | 2 | 1 | 2 | 4 | 1 | 1 | 2 |
| 1.009 | 4 | 5 | 5 | 5 | 5 | 5 | 3 | 5 | 5 | 3 | 4 | 5 |
| 1.010 | 4 | 5 | 5 | 5 | 5 | 4 | 5 | 5 | 5 | 5 | 5 | 1 |
| 1.011 | 5 | 5 | 3 | 5 | 5 | 4 | 5 | 5 | 5 | 5 | 5 | 3 |
| 1.012 | 5 | 5 | 5 | 4 | 5 | 3 | 5 | 5 | 5 | 5 | 5 | 4 |
| 1.013 | 5 | 5 | 3 | 3 | 5 | 2 | 5 | 5 | 5 | 5 | 5 | 2 |
| 1.014 | 4 | 5 | 5 | 4 | 4 | 3 | 5 | 4 | 4 | 5 | 5 | 3 |
| 1.015 | 5 | 5 | 5 | 5 | 5 | 3 | 5 | 5 | 5 | 5 | 5 | 2 |
| 1.016 | 5 | 5 | 5 | 5 | 5 | 4 | 5 | 5 | 5 | 5 | 5 | 1 |
| 1.017 | 5 | 5 | 5 | 5 | 5 | 5 | 5 | 5 | 5 | 5 | 5 | 5 |
| 1.019 | 5 | 5 | 3 | 5 | 5 | 4 | 5 | 5 | 5 | 5 | 5 | 3 |
| 1.020 | 5 | 5 | 5 | 5 | 5 | 5 | 5 | 5 | 5 | 5 | 5 | 5 |
| 1.023 | 5 | 5 | 2 | 5 | 5 | 2 | 5 | 5 | 4 | 5 | 5 | 2 |
| 1.030 | 5 | 5 | 5 | 5 | 5 | 4 | 5 | 5 | 5 | 5 | 5 | 2 |
| 1.031 | 4 | 5 | 5 | 5 | 5 | 5 | 3 | 5 | 5 | 5 | 5 | 5 |
| 1.032 | 4 | 5 | 5 | 5 | 5 | 4 | 4 | 5 | 5 | 5 | 5 | 4 |
| 1.036 | 5 | 5 | 5 | 5 | 5 | 4 | 5 | 5 | 5 | 5 | 5 | 2 |
| 1.037 | 5 | 5 | 5 | 5 | 5 | 5 | 5 | 5 | 5 | 5 | 5 | 5 |

The invention claimed is:
1. A compound of Formula (I):

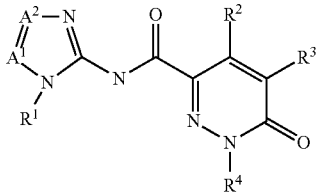

or an agronomically acceptable salt thereof,
wherein:
$A^1$ and $A^2$ are independently selected from CH and N, wherein $A^1$ and $A^2$ are not both CH;
$R^1$ is selected from the group consisting of $C_1$-$C_6$alkyl-, $C_1$-$C_6$haloalkyl- and $C_1$-$C_6$alkoxy-$C_1$-$C_3$alkyl-;
$R^2$ is selected from the group consisting of halogen, —$NHR^5$ and —O—$R^6$;
$R^3$ is selected from the group consisting of hydrogen, halogen, $C_1$-$C_6$alkyl, $C_1$-$C_6$haloalkyl-, $C_1$-$C_6$alkoxy-$C_1$-$C_3$alkyl-, benzyl and phenyl, wherein the benzyl and phenyl are optionally substituted with one or more substituents selected from the group consisting of halogen, $C_1$-$C_6$ alkyl, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-;
$R^4$ is selected from the group consisting of $C_1$-$C_6$ alkyl, $C_3$-$C_6$-cycloalkyl and $C_1$-$C_6$ haloalkyl-;
$R^5$ is selected from the group consisting of $C_1$-$C_6$alkyl-, $C_1$-$C_6$ haloalkyl-, $C_1$-$C_6$alkoxy-$C_1$-$C_3$alkyl-, benzyl and phenyl, wherein the benzyl and phenyl groups are optionally substituted with one or more substituents selected from the group consisting of halogen, $C_1$-$C_6$alkyl-, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-;
$R^6$ is selected from the group consisting of $C_1$-$C_6$alkyl, $C_1$-$C_6$haloalkyl-, $C_1$-$C_6$alkoxy-$C_1$-$C_3$alkyl; and
p=0, 1 or 2.

2. A compound according to claim 1, wherein $A^1$ and $A^2$ are both N.

3. A compound according to claim 1, wherein $R^1$ is selected from the group consisting of methyl, ethyl and propyl.

4. A compound according to claim 1, wherein $R^2$ is selected from the group consisting of hydroxyl and —$NHR^5$.

5. A compound according to claim 1, wherein $R^2$ is chlorine.

6. A compound according to claim 1, wherein $R^3$ is methyl.

7. A compound according to claim 1, wherein $R^3$ is phenyl optionally substituted with one or more substituents selected from the group consisting of halogen, $C_1$-$C_6$ alkyl, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-.

8. A compound according to claim 1, wherein $R^4$ is methyl.

9. A compound according to claim 1 wherein R1 is methyl, ethyl or propyl; R2 is chlorine, hydroxyl, or —$NHR^5$; R3 is methyl or phenyl optionally substituted with one or more substituents selected from the group consisting of halogen, $C_1$-$C_6$ alkyl, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-; and R4 is methyl.

10. A compound according to claim 1 wherein R1 is methyl, ethyl or propyl; R2 is chlorine; R3 is methyl; and R4 is methyl.

11. A compound according to claim 1 wherein R1 is methyl, ethyl or propyl; R2 is chlorine; R3 is phenyl optionally substituted with one or more substituents selected from the group consisting of halogen, $C_1$-$C_6$ alkyl, cyano, nitro, $C_1$-$C_6$ haloalkyl-, $C_1$-$C_6$alkyl-S(O)p-, aryl-S(O)p-, $C_1$-$C_6$alkoxy- and $C_1$-$C_6$haloalkoxy-; and R4 is methyl.

12. A herbicidal composition comprising a compound according to claim 1 and an agriculturally acceptable formulation adjuvant.

13. A herbicidal composition according to claim 12, further comprising at least one additional pesticide.

14. A herbicidal composition according to claim 13, wherein the additional pesticide is a herbicide.

15. A method of controlling weeds at a locus comprising application to the locus a weed controlling amount of the composition according to claim 12.

* * * * *